United States Patent
Perry

(10) Patent No.: US 11,375,719 B2
(45) Date of Patent: *Jul. 5, 2022

(54) METHOD TO INDUCE EXPRESSION OF ENZYMES THAT MODIFY PLANT DEVELOPMENT

(71) Applicant: Guenevere Diane Perry, Albany, GA (US)

(72) Inventor: Guenevere Diane Perry, Albany, GA (US)

(73) Assignee: Guenevere Perry, Sanford, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/262,004

(22) Filed: Sep. 11, 2016

(65) Prior Publication Data
US 2016/0376619 A1 Dec. 29, 2016
US 2019/0352681 A9 Nov. 21, 2019

Related U.S. Application Data

(62) Division of application No. 14/334,392, filed on Jul. 17, 2014, now Pat. No. 9,456,609.

(51) Int. Cl.
| | | |
|---|---|---|
| A01N 63/20 | (2020.01) | |
| C12P 13/00 | (2006.01) | |
| C12N 1/20 | (2006.01) | |
| C12N 1/38 | (2006.01) | |
| C12N 9/02 | (2006.01) | |
| C12N 9/78 | (2006.01) | |
| C12N 9/80 | (2006.01) | |
| C12N 9/88 | (2006.01) | |

(52) U.S. Cl.
CPC .............. *A01N 63/20* (2020.01); *C12N 1/20* (2013.01); *C12N 1/38* (2013.01); *C12N 9/0004* (2013.01); *C12N 9/78* (2013.01); *C12N 9/80* (2013.01); *C12N 9/88* (2013.01); *C12P 13/002* (2013.01); *C12P 13/004* (2013.01)

(58) Field of Classification Search
CPC .............. A01N 63/10; A01N 63/20–28; C12P 13/002–004; C12P 13/004
See application file for complete search history.

(56) References Cited

U.S. PATENT DOCUMENTS

| | | | |
|---|---|---|---|
| 8,389,441 B2* | 3/2013 | Pierce | C12N 11/06 504/117 |
| 8,992,653 B2 | 3/2015 | Smith et al. | |
| 9,554,575 B2 | 1/2017 | Smith et al. | |
| 10,004,237 B2 | 6/2018 | Pierce et al. | |
| 10,244,765 B2 | 4/2019 | Pierce et al. | |
| 2019/0133137 A1 | 5/2019 | Pierce et al. | |

FOREIGN PATENT DOCUMENTS

| | | |
|---|---|---|
| CN | 102321554 A | 1/2012 |
| WO | PCT/CA2008/00021 | 11/2008 |

OTHER PUBLICATIONS

Perry, Guenevere, "Enhancing the Expression of Enzymes Used to Degrade Hydrocarbons and Cyanohydrins in *Rhodococcus* sp. DAP 96253 by Using Inducers such as Cobalt, Urea, and Propylene Gas; Also Enhances the Ability of the Bacteria to Delay the Ripening of Several Fruit Species." Dissertation, Georgia State 2011.*
Bernard R. Glick ("Plant Growth-Promoting Bacteria: Mechanisms and Applications" Hindawi Publishing Corporation Scientifca, 2012, 1-15).*
Difco & BBL Manual (second edition (c) 2009 by Becton, Dickinson and Company Sparks, MD 21152, pp. 42-44). (Year: 2009).*
Pristijono et al. ("Effect of Continuous Exposure to Low Levels of Ethylene on Mycelial Growth of Postharvest Fruit Fungal Pathogens" Horticulturae, 2018, 4, 20, p. 1-7).*
Bradley ("Science: How ripening fruit invite fungal attack", NewScientist, Aug. 27, 1994, pp. 1-3).*
U.S. Appl. No. 12/093,779, filed Oct. 9, 2008, McGill University.

* cited by examiner

*Primary Examiner* — Paul J Holland

(57) ABSTRACT

The present invention is directed to methods of modifying the plant development process comprising of exposing a plant or plant part to volatiles biosynthesized by one or more bacteria or enzymes. Specifically, the embodiment uses one or more bacteria selected from the plant growth promoting bacteria group consisting of *Rhodococcus* spp., *Pseudomonas* spp., *Bacillus* spp., or *Xanthobacter* spp., or a mixture thereof. A closed apparatus, FIG. 1A, containing a tri-phasic system is used to expose the bacteria to hydrocarbons, iron, cyanide, and/or ammonium compounds; the method induces the biocatalyst to biosynthesize volatile compound(s) that deter ethylene production in climacteric plants or fruit resulting in the biocatalyst ability to delay fruit ripening.

4 Claims, 2 Drawing Sheets

METHOD TO INDUCE EXPRESSION OF ENZYMES THAT MODIFY PLANT DEVELOPMENT

CROSS-REFERENCE TO RELATED APPLICATIONS

Claims Benefit of Filing Date of Application: U.S. Ser. No. 14/334,392. Filed under a 37 C.F.R. § 1.53(b)

FEDERALLY SPONSORED RESEARCH OR DEVELOPMENT

Not Applicable

SEQUENCE LISTING OR A COMPUTER PROGRAM

Not Applicable

FIELD OF INVENTION

The present invention is in the field of post-harvest biotechnology. The invention generally relates to the method of exposing plant or plant parts to one or more bacteria that release volatile compounds, specifically to the bacteria ability to deter ethylene production and delay fruit ripening in climacteric plants or fruit.

The projected rise in global population raises concerns about the effectiveness of current agricultural techniques to meet the continuously growing demands for food, (Trostle and Seeley, 2013). Plant growth promoting bacteria (PGPB) may be a low cost and efficient tool to increase agricultural productivity and deter post-harvest loss. PGPB have also been used as biological fertilizers, biological pesticides, and biocatalyst to prevent post-harvest loss, (Ahemad and Kibret, 2014; Bashan 1998; Pierce et al., 2011; Perry, 2011). Several species of PGPB including Azobacter, *Bacillus, Azosprillum, Acetobacter, Pseudomonas*, and *Rhodococcus* species these bacteria have been used for centuries as bacterial inoculants to modify plant development and improve nutrient uptake for plant cells, (Bashan, 1998; Vacheron et al., 2013). Ethylene production regulates plant development in climacteric fruit. Controlling ethylene concentrations can deter the plant development process and retard fruit ripening, (Binder et al., 2004; Burg, 1973; Trobacher, 2009; Victor et al., 2012; Yip and Yang, 1988; Yang and Oetiker, 1998). PGPB modify plant development by degrading ethylene, degrading ethylene precursors, and/or producing compounds that inhibit auxin production in plant cells, (Allen and Ensign, 1998; Arshad et al., 2007; DeBont and Albers, 1976; Dhungana et al., 2007; Elsgaard, 1998; Glick, 2012; Kloepper et al., 1991; Penrose and Glick, 2003). Plant growth promoting bacteria can also use dehydratase and nitrile degrading enzymes to biosynthesize cyanohydrins or auxins that manipulate the plant development process, (Egamberdieva, 2012; Hayat et al., 2010; Nomura et al., 2012; Kato et al., 2004).

A previous method to induce bacteria to delay fruit ripening was developed by Pierce et al., 2011 and U.S. patent 2013/0274, 102 (2013). Bacteria were induced to delay fruit ripening after prolonged exposure to cobalt, urea, and/or asparagine. The cell paste was immobilized on cellulose material and placed on or near fruit to delay climacteric ripening. This method was arduous and laborious; the induction process lasted for a 13-14 day period. This method would be very costly to translate into actual manufacturing and industrial applications. The multiple culture steps, expensive equipment, and expensive materials, including urea and glucose, would drive-up production cost and reduce profits.

The new method I developed exposes PGPB to hydrocarbons, iron, and ammonium compounds to enhance the bacteria ability to delay fruit ripening. My method requires fewer media transfers and samples are ready in half the time. The new method translates into reduced production and labor cost and increased reproducibility of results, improving the inventions relevance for industrial and manufacturing applications. Biocatalyst exposed to inducers were able to modify the plant development process and delay the effects of fruit ripening, including changes in hue, texture, firmness, reduced presence of brown spotting, and reduced fungal infection.

BRIEF SUMMARY OF INVENTION

In accordance with one embodiment, the new method is directed to the use of short chain hydrocarbons, including but not limited to propylene (propene) and/or ethylene to induce PGPB. The additional necessary media components include heavy metals, including but not limited to iron, and ammonium compounds to induce biocatalyst ability to modify plant development in climacteric fruit.

The PGPB are referred to as a biocatalyst comprising of one or more bacteria, particularly *Rhodococcus* or *Norcardia* spp., or a mixture thereof. The biocatalyst, comprising of PGPB include but is not limited to *Acetobacter, Azobacter, Azosprillum, Bacillus, Brevibacterium, Norcardia, Pseudomonas, Rhodococcus*, or *Xanthobacter* spp. that can catalyze the hydrocarbon into volatile compounds that deter ethylene production in climacteric plants or fruit.

The present new invention method occurs wherein the biocatalyst are cultivated in a closed tri-phasic system apparatus described herein. This invention further provides an apparatus used to facilitate the induction of PGPB to produce volatile compounds required to modify the plant development process and delay ripening in climacteric plants or fruit.

BRIEF DESCRIPTION OF THE DRAWINGS

The invention was described above in broad terms, reference will now address the accompanying drawing, this drawing is not necessarily drawn to scale, and wherein.

DETAILED DESCRIPTION

Figure 1A:
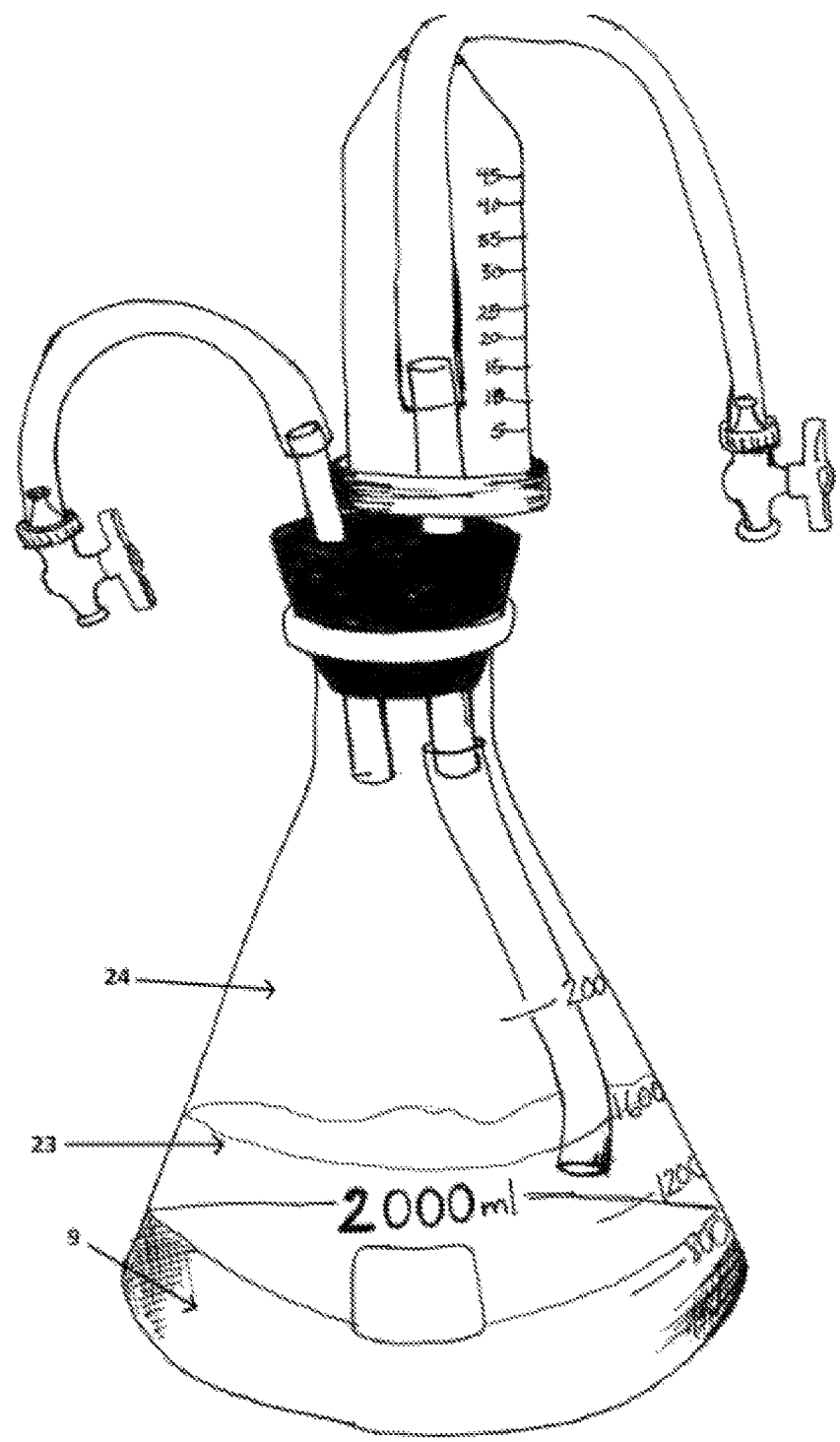
FIG. 1A is a perspective front view of the apparatus of the past invention; the apparatus contains a tri-phasic system comprised of a solid, liquid, and gaseous phase labeled 9, 23, and 24 respectively.
Figure 1B:
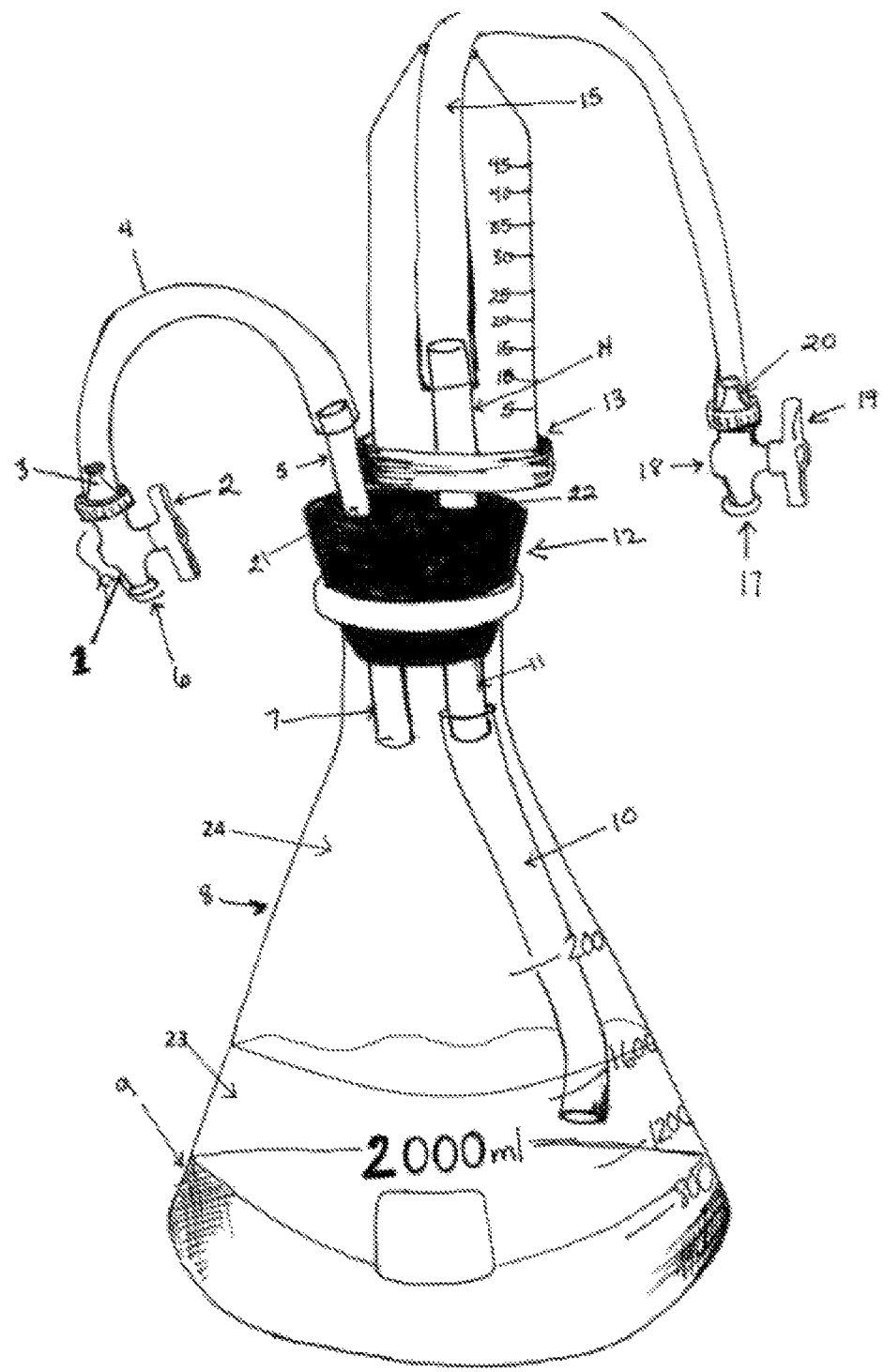
FIG. 1B is a detailed operational view of the proportion indicated by the section lines 2-3 in FIG. 1, a closed system apparatus of the present invention; the apparatus contains a tri-phasic system. The biocatalyst is maintained in the solid and liquid phase of the system as defined herein below, and comprises one or more of the microorganism of the invention.

FIGS. 1A and 1B—First Embodiment

The inventor has discovered a method to induce plant growth promoting bacteria to perform as a biocatalyst that are capable of converting short chained hydrocarbons into volatile compounds that manipulate the plant development process and delay fruit ripening. This detailed description should not be considered a means of limiting this invention to a particular embodiment. The description contains the word "comprising", or grammatical variations of the word, it is understood to imply inclusion rather than limitations. The one or more bacteria used in the methods and apparatuses of the invention may at times be more generally referred to herein as the "biocatalyst." The hydrocarbons are aliphatic gaseous compounds, including but not limited to propylene (propene) and/or ethylene compound or mixture thereof. The volatile compounds produced from the reaction, include but are not limited to nitriles and/or cyanohydrin mixture or combination thereof. The bacteria also uptake additional compounds released by plant cells during the induction process, including cyanide. The induction process also induces and stabilizes several enzymes found in *Rhodococcus* or *Norcardia*, including but not limited to nitrile degrading enzymes and/or monooxygenase or a combination thereof within the bacteria. The present invention is described in full detail herein after; references are made to embodiments included in this application.

Elements to monitor the efficiency of the biocatalyst can be attached to the apparatus to monitor carbon dioxide levels or pH levels in the media. Conversion of hydrocarbons to volatile compounds in a biocatalyst may comprise of additional features to permit continued circulation of air flow within the closed system. An individual skilled in the art could envision modifications for the apparatus to improve monitoring and controlling of the atmospheric conditions for the biocatalyst.

One embodiment of the closure is illustrated in FIG. 1A (front view) and FIG. 1B (detailed operational view). In particular embodiments of the invention the biocatalyst are cultivated in a closed flask container, providing a closed system. For example, as shown in FIG. 1A, the apparatus contains a tri-phasic system comprised of a solid, liquid, and gaseous phase. The solid phase (9) is comprised of 12 g of Bacto agar suspended into 300 ml of dH2O, autoclaved and cooled in a 2 L Erlenmeyer flask. However the solid phase can consist of any of a gelatinous structure, bead-like structure, and/or a matrix like structure that can support microbial cells and facilitate filamentous growth. The liquid phase (23) contains 300 ml of the induction media that consist of a heavy metal, ammonium chloride, and phosphate compounds. The gaseous headspace (24) was filled with 10-15% of hydrocarbon gas for 3-5 days at 30° C. and 120 rpm. The gaseous compounds can include ethylene and/or propylene.

Operation

First Embodiment FIG. 1B

A detailed operational view of the apparatus used for the cultivation of biocatalyst, shown in FIG. 1B. The apparatus is 2 L Erlenmeyer flask (8), apparatus could consist of any closed system container that could support a tri-phasic system. The rubber stopper (12) prevented loss of gaseous media components. The agar base (9) provides a solid surface for biofilm formation; the solid phase is an essential component to enhancing bacteria ability to modify plant development. The liquid phase (23) contains induction media necessary to induce bacteria ability to modify plant development. The gaseous headspace (24) contains hydrocarbon gas, an essential inducer to enhance bacteria ability to modify plant development.

Headspace Collection—FIG. 1B

Gaseous components are added and removed from the headspace using a two way valve (1). The open/close flow and direction of the valve is controlled by knob (2). The entry port (6) is used to attach syringes to inject gas into the system, media or gas enters the connecting tubing through the exit port (3). The 3/16 inch rubber tubing (4), is used throughout the system, the tubing is flexible and autoclavable. Cells pass quickly through the rubber tubing with little resistance or backflow. The rubber tube is connected to ⅛ silicon tube (5), silicon is rigid and necessary for constructing entry and exit point through the holes (21) in the rubber stopper. Gas enters the headspace (7).

Sample Collection—FIG. 1B

Gaseous and liquid components are added and removed through a two way valve (18). The open/close flow and direction of the valve is controlled by knob (19). The entry port (17) is used to attach syringes to inject liquid media into the system, enters the connecting tubing through the exit port (20). The 3/16 inch rubber tubing (15) is used throughout the system. The rubber passes into a 50 ml falcon tube (13) and is loosely connected to ⅛ silicon tube (14). The falcon tube (13) acts as a reservoir for over flow during cultivation, exposed openings are sealed with silicon-based epoxy. The ⅛ silicon tube (14) are inserted into the stopper hole (22). A portion of the silicon tubing enters the flask (11) and connects to 3/16 inch rubber tubing (10). The rubber tubing is perforated on the ends and slightly coiled into the medium to allow for direct bubbling of gaseous components into the medium.

The present invention is generated in a closed system apparatus, comprising of a tri-phasic media condition. The tri-phasic condition consists of a solid porous base, aqueous phase, and a gaseous phase composed of a hydrocarbon and air mixture. The mechanism used for induction of the biocatalyst is not intended to be limiting by a particular enzyme, but may increase activity or expression of one or more enzymes, comprising of dehydratase, nitrile degrading enzyme, and/or monooxygenase, or a mixture thereof. The induction of one or more of these enzymes may play a role conversion of a hydrocarbon to a volatile compound by the biocatalyst. This present invention encompasses biocatalysts that produce, or are induced to produce, or are genetically modified to produce dehydratase, nitrile degrading, and/or monooxygenase enzyme, at a quantity or at an enzymatic activity level sufficient for the conversion of short chained hydrocarbons to volatile compounds that deter ethylene production in climacteric plants or fruit. These enzymes have been studied in depth in literature-based publications, possessing recognized enzymatic activities. The abundance of reference material related to the enzymes assures that such enzymes are well known to individuals skilled in the art, and the enzymes discussed in this invention can be easily produced, engineered, or purified from the biocatalyst.

The following embodiments are offered as examples, and are felt to be non-limiting and are meant to illustrate the invention but are not meant to be limiting in any way.

A working example of the invention is shown in Perry, G. D. 2014. Ethylene induced soil microbes to increase seed germination, reduce growth time, and improve crop yield in *Pisum sativum* L. PeerJ PrePrints 2:e543v1

CONCLUSION, RAMIFICATIONS, AND SCOPE

Accordingly the reader will see that, according to one embodiment of the invention, I have developed a low cost method to expose PGPB to hydrocarbons and heavy metal compounds to induce bacteria to modify the plant development process and delay fruit ripening in climacteric fruit and plants. While the above description contains many specifications, these should not be construed as limitations on the scope of any embodiment, but as exemplifications of the presently preferred embodiments thereof. Many other ramifications and variations are possible within the teachings of various embodiments.

The invention claimed is:

1. A method of reducing fungal infections in climacteric fruit or plants comprising:
   inducing bacteria of the genus *Rhodococcus*, genus *Pseudomonas*, genus *Bacillus*, genus *Xanthobacter* to express dehydratase, nitrile hydratase and monooxygenase enzymes by culturing the bacteria under an atmosphere comprising ethylene and/or propylene with the co-inducers iron and urea and wherein no cobalt is present, and wherein the bacteria convert the ethylene and/or propylene into volatile compounds,
   applying the resulting volatile compounds either directly or indirectly to climacteric fruit or plants in order to reduce fungal infection.

2. The method of claim 1, wherein the bacteria include *Rhodococcus rhodochrous* DAP 96253.

3. The method of claim 1, wherein the volatile compounds consist essentially of nitriles and/or cyanohydrin.

4. The method of claim 1, wherein the climacteric fruit or plants are a climacteric fruit and a non-climacteric plant.

* * * * *